(12) United States Patent
Mukasa et al.

(10) Patent No.: US 6,386,872 B1
(45) Date of Patent: May 14, 2002

(54) CAPSULE FOR DENTAL RESTORATION MATERIAL

(75) Inventors: Yoshihisa Mukasa; Yoshimasa Suzuki; Shuji Aoyagi, all of Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/752,676

(22) Filed: Jan. 3, 2001

(51) Int. Cl.[7] ................................. A61C 5/04
(52) U.S. Cl. ................. 433/90; 206/63.5; 206/219; 222/136; 222/570
(58) Field of Search ............... 433/90, 89; 206/63.5, 206/219, 222; 222/136, 570; 604/218, 311

(56) References Cited

U.S. PATENT DOCUMENTS

| | | | | |
|---|---|---|---|---|
| 2,754,590 A | * | 7/1956 | Cohen | 433/90 |
| 3,028,052 A | * | 4/1962 | Archer | 222/136 |
| 3,648,899 A | * | 3/1972 | Lukesch et al. | 222/136 |
| 3,684,136 A | * | 8/1972 | Baumann | 222/386 |
| 4,941,751 A | * | 7/1990 | Muhlbauer | 206/63.5 |
| 5,026,283 A | * | 6/1991 | Osanai et al. | 433/90 |
| 5,275,312 A | * | 1/1994 | Labruzzo | 222/570 |
| 6,135,771 A | * | 10/2000 | Dragan et al. | 433/90 |

* cited by examiner

*Primary Examiner*—John J. Wilson
(74) *Attorney, Agent, or Firm*—Oblon, Spivak, McClelland, Maier & Neustadt, P.C.

(57) ABSTRACT

A capsule contains dental restoration material for applying directly to a site to be restored. A capsule main body has a mixing compartment for a powder component and a first aperture forming portion to form an outlet hole. A liquid cup has a compartment for a liquid component and a second aperture forming portion to form an outlet hole for the liquid component. A stopper is provided on an external surface near a rear end portion for inhibiting sliding of the cup into the main body while the second aperture forming portion is being broken through, but not inhibiting the cup to slide into the main body when a large force is applied. A plunger has a projection for breaking through the second and first aperture forming portions. A nozzle has a rear end portion with a shape corresponding to the tip portion of the main body.

7 Claims, 2 Drawing Sheets

CAPSULE FOR DENTAL RESTORATION MATERIAL

BACKGROUND OF THE INVENTION

1. Field of the Invention

The present invention relates to a capsule for dental restoration material, which can be applied to a site to be restored of a tooth, immediately after mixing a dental restoration material comprising two components of a powder component and a liquid component, in filling, cementing, lining and other applications for restoration of the teeth in the dental remedy field.

2. Description of the Conventional Art

In general, a dental restoration material is used for restoration of the teeth. As the dental restoration material, a two-component system material comprising a powder component and a liquid component, which are reacted with each other upon mixing, is usually used. Hitherto, this two-component system material was provided for use after appropriately weighing the powder component and the liquid component every time and mixing them with each other. However, in recent years, for the purposes of omitting a weighing operation of the powder component and the liquid component and an operation for accommodating the dental restoration material after mixing into a syringe for applying it to a site to be restored, there have been developed capsules for dental restoration material, in which certain amounts of the powder component and the liquid component are previously weighed and accommodated in an isolated state from each other, the isolated state is released at a desired time, the both components are mechanically mixed with each other by a mixer or the like, and the resulting mixed material is extruded and applied directly into a site to be restored, such as a tooth cavity, through a nozzle.

For example, in a capsule as disclosed in Japanese Patent Publication No. 38853/1991, a powder component of two components is accommodated in a mixing compartment of a container main body, and the other liquid component is charged in a bag, which is assembled in a side portion of the mixing compartment accommodating the powder component by means of a clip. The container main body has an aperture in a tip portion. This aperture can be clogged in a spherical bearing portion in a rear end portion of a distribution nozzle. Further, the distribution nozzle is kept from the outside by means of a separately formed cap, thereby preventing the powder component to leak to the outside of the mixing compartment. And, at the time of use, the clip is pushed down in a direction of the mixing compartment using a separately prepared exclusive tool, thereby smashing and breaking the bag having a liquid component charged therein; the liquid component is discharged into an interior of the mixing compartment through an aperture provided on a side wall of the mixing compartment, followed by shaking by a mixer, thereby mixing the liquid component and the powder component with each other; the spherical bearing portion in the rear end portion of the distribution nozzle is then rotated to release a passage of the distribution nozzle; and the mixed material is extruded from the distribution nozzle via a separately prepared tool by means of a pushing pressure of a piston.

In the capsule having the structure described above, as a material of the bag having a liquid component charged therein, a laminate sheet comprising an aluminum foil and a resin film is generally used. For this reason, there are various problems as follows. That is, there is a high risk that in the case where the liquid component is acidic, at the time of use, the liquid component which has flown out by the breakage of the bag dissolves the aluminum foil in an exposed broken section of the bag and mingles into the dental restoration material. Further, there may be a risk that since the bag having a liquid component charged therein is broken by a mechanical pushing pressure, a residual piece of the broken bag section faced at the aperture of the mixing compartment mingles into the mixing compartment. Still further, since the aperture on the wall of the mixing compartment having a powder component accommodated therein is clogged merely by pushing the bag having a liquid component charged therein by the clip, the sealing properties of the mixing compartment is not complete, and an exclusive tool is necessary for breaking the bag. Also, since in the distribution nozzle assembled in the tip side of the mixing compartment, an angle against the container main body is limited to a constant angle in order to ensure a passage of the mixed material, it lacks a degree of freedom, and it is impossible to exchange the distribution nozzle.

On the other hand, a two-component system capsule for mixing and discharge as disclosed in Japanese Patent Laid-Open No. 268555/1987, in which a powder component of two components is accommodated in a mixing compartment within a container main body, and the other liquid component takes a form (pillow) being wrapped by a sheet film comprising a resin, a metal foil, or a laminate comprising a resin and a metal foil. In this pillow, the strength in the main body side is previously set to be low, and a cap to be screw engaged with the container main body is assembled in the tip side of the container main body. At the time of use, when the cap is strongly screw engaged with the container main body and moved, the sheet in the container main body side of the pillow is broken, and the liquid component is introduced into the mixing compartment through an aperture provided on a center axis of the tip of the container main body, whereby it is mixed with the powder component. After the mixing, a through rod set within a nozzle provided on an extension line of the center axis of the cap is pushed in and breaks through the sheet of the pillow in the cap side, i.e., in the nozzle side, to form a discharge outlet for the mixed material. Thereafter, the through rod is removed, a piston set in an interior of the rear end portion of the container main body is moved into the tip portion side of the container main body, and the mixed material in the mixing compartment is discharged through the nozzle.

The capsule for mixing and discharge having the structure as described above involves the following problems. That is, like the case of Japanese Patent Publication No. 38853/1991, since the sheet using a metal foil or the like wrapping the liquid component is squashed by force by means of a mechanical external pressure, thereby mixing the liquid component with the powder component in the mixing compartment, there is a risk that the liquid component dissolving an aluminum in broken section of the sheet therein mingles into the dental restoration material. Further, there may be a risk that a broken piece of the sheet mingles into the dental restoration material during the rupture of the pillow by a pushing pressure, the breakthrough of the pillow by the through rod, and the discharge of the mixed material. In addition, in such a structure, the pillow having a liquid component accommodated therein is located in a second cell between the tip portion of the mixing compartment and the nozzle. For this reason, in the case where the squash of the pillow is incomplete due to inexperience in the operation, or the like, there is a risk that the liquid component remains within the pillow, and the mixed material and the liquid component are extruded in a separated state at the tip or external surface of the mixed material during the discharge of the mixed material, whereby the desired performance is not likely obtained. Moreover, with respect to the operability, there is a defect that the operation is complicated because for the discharge of the mixed material, the through rod must be removed prior to the discharge, after the pillow is broken through by the through rod being pushed into the sheet having a higher strength of the pillow.

Further, like the case of Japanese Patent Laid-Open No. 268555/1987 as cited above, Japanese Patent Laid-Open No. 43653/1988 discloses a capsule for dental restoration material in which a liquid component pack having a liquid component packed by a sheet such as an aluminum foil is aligned in an outside of the tip of the mixing compartment of the container main body; the liquid component pack is ruptured by a screw-in pushing pressure of the cap, thereby making the liquid component flow into the mixing compartment through an aperture on the center axis of the container main body and mix with the powder component; and a plunger with a tool for breakthrough of a pack provided in the rear end portion of the container main body is moved to break through a tip of the liquid component pack in the nozzle side, thereby supplying a mixed dental restoration material into a dental restoration portion. However, in this capsule, like the above-described two structures, since the liquid component pack having the liquid component wrapped by a sheet such as an aluminum foil is used, this capsule involves the following problems. That is, when the liquid component pack is pushed and ruptured, the liquid component in which the aluminum in the broken section of the sheet constituting the liquid component pack is dissolved likely mingles into the dental restoration material, and a broken piece of the liquid component pack likely mingles into the dental restoration material. Further, since the liquid component pack is located forward of the mixing compartment of the container main body, in the case where the pushing pressure is insufficient, the liquid component does not completely enter into the mixing compartment, whereby the mixing cannot be thoroughly effected. Besides, not only the liquid component remained within the liquid component pack is extruded in a separated form from the mixed material during the discharge of the mixed material, but also in a state before mixing the two components of the powder component and the liquid component, the aperture of the mixing compartment is clogged merely by means that it has come into contact with a surface having a weak strength of the liquid component pack, whereby the powder component possibly leaks out.

SUMMARY OF THE INVENTION

The invention is aimed to overcome the problems of the conventional art capsules for dental restoration material as described above and provide a capsule for dental restoration material that is free from defects including dissolution of a broken metal section of a sheet constituting a pack accommodating a liquid component of the capsule for dental restoration material by the liquid component, contamination of a broken piece of the pack as a foreign matter into the dental restoration material by pushing rupture, and retention of the liquid component within the pack by insufficient pack pushing pressure, and that is improved in the sealing properties of a mixing compartment accommodating a powder component, is small-sized, is extremely simple in the structure, is less in the number of parts, and can be operated with ease.

In order to solve the above-described problems of the conventional art, we, the present inventors made extensive and intensive investigations. As a result, it has been found that a capsule for dental restoration material for applying directly to a tooth site to be restored of a patient a mixed material prepared by mixing therein a dental restoration material comprising two components of previously weighed constant amounts of a powder component and a liquid component, having a structure comprising a capsule main body in a cylindrical shape having a mixing compartment accommodating a powder component therein, the capsule main body being provided with a first aperture forming portion to form an outlet hole for the mixed material on a center axis in a tip portion thereof; a liquid cup having a liquid component accommodation compartment accommodating a liquid component therein, the liquid cup being provided with a second aperture forming portion to form an outlet hole for the liquid component on a center axis in a tip portion thereof, being engaged with a cylindrical portion to form the mixing compartment of the capsule main body, and being provided on an external surface in the vicinity of a rear end portion thereof with a convex stopper having a size so as to inhibit the liquid cup to readily slide into the capsule main body during breaking through the second aperture forming portion to form the outlet hole for the liquid component but not inhibit the liquid cup to slide into the capsule main body when a large force is applied; a plunger having a rod-like projection for breaking through the second aperture forming portion of the liquid cup and the first aperture forming portion of the capsule main body, the plunger being engaged with a cylindrical portion with in the liquid cup; and a nozzle whose rear end portion has a shape corresponding to the tip portion of the capsule main body, the nozzle being connected to the tip portion of the capsule main body, prevents a phenomenon that the liquid component dissolves a metal of a broken section of a pack, contamination of a broken piece of the pack into the dental restoration material, and retention of the liquid component within the pack, because the pack accommodating a liquid component is not used, improves the sealing properties of the mixing compartment accommodating the liquid component therein, is small-sized and simple in the structure, is less in the number of parts, and enables to perform the dental restoration remedy with an easy operation, leading to the accomplishment of the present invention.

And, it has been found that the following embodiments are preferred. That is, when an applier engagement groove is engraved on an outer periphery side surface in the vicinity of the rear end portion of the capsule main body, it is possible to easily perform an operation in which a claw of the applier is engaged with the applier engagement groove, and the plunger is moved by a push rod of the applier, thereby making the powder component flow completely into the mixing compartment and an operation in which the mixed material as prepared by mixing the liquid component and the powder component with each other is extruded from the nozzle. When the outlet hole of the first aperture forming portion of the capsule main body and the outlet hole of the second aperture forming portion of the liquid cup are a circular hole, respectively, and a notch having a size of about three-fourth of the circumference is provided in each periphery thereof, during breaking through the aperture forming portions of the capsule main body and the liquid cup by the rod-like projection of the plunger, the whole of the aperture forming portions can be broken through with a small force without causing cut-off. Further, when the tip portion of the nozzle is tapered and curved, the mixed material can be fed into a desired small site such as a tooth cavity, without forcing a patient to open a mouth largely. Still further, when the rear end portion of the nozzle is connected to the tip portion of the capsule main body by means of an engagement of a ring-like convex portion with a ring-like concave portion having a corresponding shape thereto, the nozzle can be conveniently rotated against the capsule main body.

DESCRIPTION OF THE PREFERRED EMBODIMENTS

Embodiments of the capsule for dental restoration material according to the present invention will be described in detail with reference to the drawings.

Figure 1:
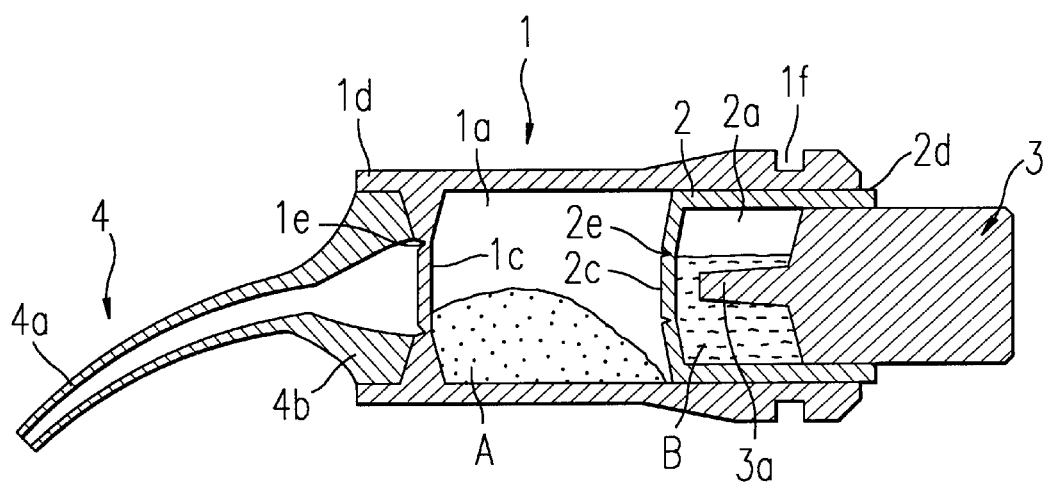
FIG. 1 is a side cross-sectional view for explaining one embodiment of the capsule for dental restoration material according to the present invention.
Figure 2:
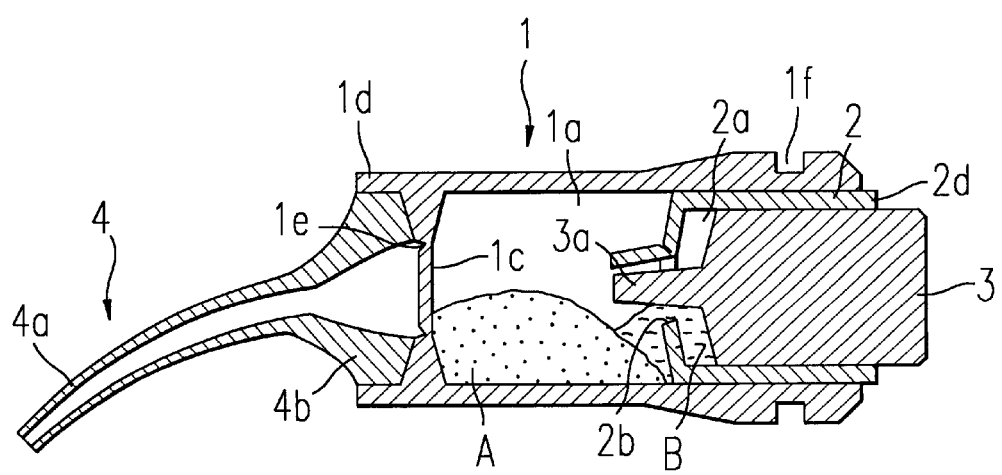
FIG. 2 is a side cross-sectional view for explaining a state of starting the mixing in the capsule for dental restoration material of FIG. 1.
Figure 3:
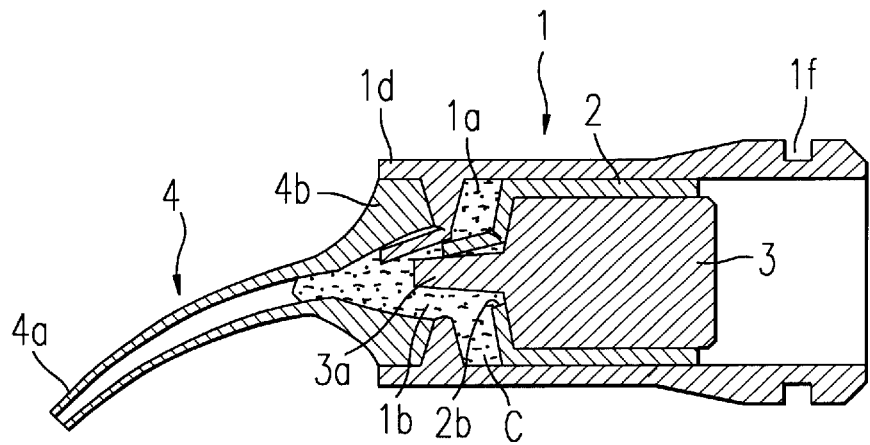
FIG. 3 is a side cross-sectional view to show an extrusion state of a mixed material in the capsule for dental restoration material of FIG. 1.
Figure 4:
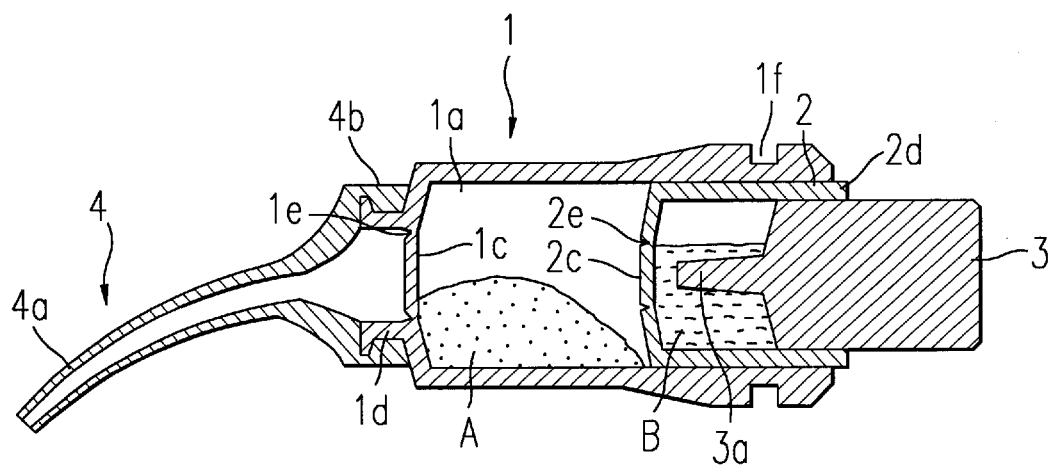
FIG. 4 is a cross-sectional view to show another embodiment of the capsule for dental restoration material according to the present invention.

FIG. 1 is a side cross-sectional view for explaining one embodiment of the capsule for dental restoration material according to the present invention; FIG. 2 is a side cross-sectional view for explaining a state of starting the mixing in the capsule for dental restoration material of FIG. 1; FIG. 3 is a side cross-sectional view to show an extrusion state of a mixed material in the capsule for dental restoration material of FIG. 1; and FIG. 4 is a cross-sectional view to show another embodiment of the capsule for dental restoration material according to the present invention.

In the drawings, a numeral 1 is a monolithically molded synthetic resin-made cylindrical capsule main body, in which a powder component A is previously accommodated and which is provided with a mixing compartment 1a for mixing the powder component A with a liquid component B when the liquid component B has flown thereinto. The capsule main body 1 is also provided with a first aperture forming portion 1c to form an outlet hole 1b for a mixed material C comprising the powder component A and the liquid component B mixed with each other on a center axis in a tip portion 1d thereof. The capsule main body 1 has a shape corresponding to a nozzle 4 as described later on an external surface of the tip portion 1d, to which the nozzle 4 is connected. In this connection, it is preferred that an applier engagement groove 1f is engraved on an outer periphery side surface in the vicinity of a rear end portion of the capsule main body 1. Further, it is preferred that the capsule main body 1 is constituted of a resin which will not impair the characteristics of the powder component A within the mixing compartment 1a.

A numeral 2 is a monolithically molded synthetic resin-made cylindrical liquid cup having a liquid component accommodation compartment 2a in which the liquid component B is accommodated. The liquid cup 2 is provided with a second aperture forming portion 2c to form an outlet hole 2b for the liquid component B on a center axis in a tip portion thereof, is engaged with a cylindrical portion for forming the mixing compartment 1a of the capsule main body 1, and is provided on an external surface in the vicinity of a rear end portion thereof with a convex stopper 2d having a size so as to inhibit the liquid cup 2 to readily slide into the capsule main body 1 during breaking through the second aperture forming portion 2c to form the circular hole 2b for the outlet of the liquid component B but not inhibit the liquid cup 2 to slide into the capsule main body 1 when a large force is applied. It is preferred that the liquid cup 2 is constituted of a resin which will not impair the characteristics of the liquid component B accommodated therein.

A numeral 3 is a plunger having a rod-like projection 3a for breaking through the second aperture forming portion 2c to form the outlet hole 2b of the liquid cup 2 and the first aperture forming portion 1c to form the outlet hole 1b of the capsule main body 1, which is engaged with a cylindrical portion within the liquid cup 2. It is preferred that the plunger 3 is constituted of a resin which will not impair the characteristics of the liquid component B accommodated in the liquid cup 2.

A numeral 4 is a nozzle, in which a rear end portion 4b thereof has a shape corresponding to the tip portion 1d of the capsule main body 1 such that the rear end portion 4b can be connected to the external surface of the tip portion 1d of the capsule main body 1. It is preferred that a tip portion 4a of the nozzle 4 is tapered and curved such that it is easy to apply the dental restoration material to a site to be restored of a patient.

Next, a method for use of the capsule for dental restoration material according to the present invention, which comprises the above-described constituting members, will be described below.

In the capsule for dental restoration material according to the present invention, the liquid cup 2 having a constant amount of the liquid component B accommodated in the liquid accommodation compartment 2a and sealed by the plunger 3 is engaged with an aperture in the rear end side of the capsule main body 1 having a constant amount of the powder component A accommodated in the mixing compartment 1a, and the rear end portion 4b of the nozzle 4 is connected to the external surface of the tip portion 1d of the capsule main body 1 (see FIG. 1).

In order to use the capsule for dental restoration material according to the present invention constituted as above, first of all, the plunger 3 engaged in the rear end side of the liquid cup 2 that is engaged in the rear end side of the mixing compartment 1a of the capsule main body 1 is forced by a finger or the like until the tip of the plunger 3 has reached an internal surface of the tip portion of the liquid cup 2 and stopped. By this operation, the second aperture forming portion 2c on the center axis in the tip portion of the liquid component accommodation compartment 2a of the liquid cup 2 is broken by the rod-like projection 3a of the plunger 3, thereby the outlet hole 2b being opened, and the liquid component B is made flow completely into the mixing compartment 1a having the powder component A accommodated therein through the outlet hole 2b (see FIG. 2). During this period, since the convex stopper 2d is provided on the external side surface in the vicinity of the rear end portion of the liquid cup 2 and the convex stopper 2d is engaged with the rear end portion of the capsule main body 1, the liquid cup 2 does not enters into the capsule main body 1. In this connection, during breaking through the second aperture forming portion 2c of the liquid cup 2 by the rod-like projection 3a of the plunger 3, when the outlet hole 2b is in a thin-film state or circular and a notch 2e having a size of approximately three-fourth of the circumference is provided, not only it can be easily broken through, but also cut-off of the whole from the liquid cup 2 can be prevented.

Thus, after the liquid component B has completely flown from the liquid component accommodation compartment 2a into the mixing compartment 1a, the capsule for dental restoration material according to the present invention is separately installed into an exclusive mixer, thereby mixing the powder component A and the liquid component B to form a mixed material C. When the mixing of the powder component A and the liquid component B are completed, a shoulder portion in the vicinity of the tip portion of the capsule main body 1 is engaged with an applier. Alternatively, in the case where the applier engagement groove If is engraved on the outer periphery side surface in the vicinity of the rear end portion of the capsule main body 1, a claw (not shown) of the applier is engaged with the applier engagement groove if. Then, the plunger integrated with the liquid cup 2 is moved to a tip direction within the capsule main body 1 by means of a push rod of the applier. By this operation, the first aperture forming portion 1c on the center axis in the tip portion of the capsule main body 1 is broken through by the rod-like projection 3a of the plunger 3 to open the outlet hole 1b, whereby the mixed material C flows into the nozzle 4 through the outlet hole 1b (see FIG. 3). In this connection, during breaking through the first aperture forming portion 1c of the capsule main body 1 by the rod-like projection 3a of the plunger 3, when the outlet hole 1b is in a thin-film state or circular and a notch 1e having a size of approximately three-fourth of the circumference is provided, not only it can be easily broken through, but also cut-off of the whole from the capsule main body 1 can be prevented.

In such a state, when the tip portion 4a of the nozzle 4 is pushed to a tooth site to be restored of a patient, and the applier is operated, thereby the plunger 3 integrated with the liquid cup 2 being further moved to the tip direction within the capsule main body 1, the mixed material C is extruded from the tip portion 4a of the nozzle 4 and filled in the tooth site to be restored.

In the embodiment as shown in FIGS. 1 to 3, the nozzle 4 has a shape in which the tip portion thereof is tapered and curved, has also a shape corresponding to the tip portion 1d of the capsule main body 1, and is connected to the tip portion 1d of the capsule main body 1 by means of weld fixing. In this case, the connection of the nozzle 4 to the capsule main body 1 is not particularly limited, but any of weld fixing by means of supersonic, laser, high frequency, or the like as in the above-described embodiment, adhesion fixing with an adhesive, and screw fixing by forming a screw portion can be employed as the fixing method.

Further, as shown in FIG. 4, when employing a method in which a ring-like convex portion is provided on an outer periphery of the tip portion 1d of the capsule main body 1, a ring-like concave portion having a shape corresponding thereto is provided in the rear end portion 4b of the nozzle 4, and the ring-like convex portion is engaged with the ring-like concave portion by means of an elasticity of the capsule main body 1 and/or the nozzle 4, thereby effecting the connection, the nozzle 4 is rotatable around the tip portion 1d of the capsule main body 1, so that the direction of the tip portion 4a of the nozzle 4 can be changed depending upon a site to apply, or the nozzle 4 can be removed from the capsule main body 1 and replaced by the other nozzles 4 suitable to use for various tooth sites to be restored of patients.

As such a modification of the structure, in FIG. 4, a ring-like convex portion may be provided on an outer periphery in the rear end portion 4b of the nozzle 4, whereas a ring-like concave portion having a shape corresponding to the outer periphery may be provided in the tip portion 1d of the capsule main body 1. Further, in FIG. 1, a ring-like convex portion may be provided on an outer periphery of the rear end portion 4b of the nozzle 4, whereas a ring-like concave portion having a shape corresponding to the inner periphery may be provided in the tip portion 1d of the capsule mainly body 1.

As described above in detail, since the capsule for dental restoration material according to the present invention does not use a liquid component pack in which an aluminum foil is used for accommodating a liquid component, as in the capsules as disclosed in Japanese Patent Publication No. 38853/1992, Japanese Patent Laid-Open No. 268555/1987, and Japanese Patent Laid-Open No. 43653/1988, it can not only prevent the liquid component having aluminum dissolved therein to mingle into the dental restoration material but also prevent a broken piece of the liquid component pack formed by pushing rupture to mingle into the dental restoration material. Further, the capsule for dental restoration material according to the present invention is free from a risk that the liquid remains within the liquid component pack, whereby the mixed material and the liquid are discharged in a separated state from each other. Moreover, during use of the capsule for dental restoration material according to the present invention, the mixed material can be applied directly a tooth site to be restored, such as a cavity, by a simple operation comprising a step for forcing the plunger by a finger or the like, a step for mixing the powder component and the liquid component with each other by means of a mixer, and a step for extruding the mixed material after setting it in the applier. Still further, since the capsule for dental restoration material according to the present invention does not at all use a material that is likely dissolved in the liquid component, such as an aluminum, there is an advantage in the storage stability over a long period of time. Even further, in the capsule for dental restoration material according to the present invention, a nozzle can be replaced to the one having an optimum shape depending on the necessity in use for the dental restoration every time, by employing a method in which the rear end portion of the nozzle is connected to the tip portion of the capsule main body through an engagement of the ring-like convex portion with the concave portion having a shape corresponding to the inner periphery.

In addition, the capsule for dental restoration material according to the present invention has other various advantages as follows. That is, it requires neither an exclusive tool for pushing rupture of the liquid component pack nor an operation of pulling out the nozzle, as required in the capsule disclosed in Japanese Patent Publication No. 38853/1992; it is free from an operation of pushing rupture of the liquid component pack by twisting the cap, an operation of breaking through the liquid compartment pack by forcing the push rod installed within the nozzle, and an operation of drawing out the push rod before the discharge of the mixed material, as seen in the capsule disclosed in Japanese Patent Laid-Open No. 268555/1987; and it is free from an operation of pushing rupture of the liquid component pack by twisting the cap, as seen in the capsule disclosed in Japanese Patent Laid-Open No. 43653/1988.

Also, since the capsule for dental restoration material is of a disposable type, which is disposed after the remedy of each patient, the capsule for dental restoration material according to the present invention is less in the number of parts as compared with the conventional art capsules for dental restoration material, and hence, it can reduce the amount of wastes and contribute to environmental improvements.

In the light of the above, the capsule for dental restoration material according to the present invention, which has various advantages, is greatly valuable in contribution to the dental field.

While the present invention has been described in detail and with reference to specific embodiments thereof, it will be apparent to one skilled in the art that various changes and modifications can be made therein without departing from the spirit and scope thereof.

What is claimed is:

1. A dental restoration device for applying a mixed dental restoration material directly to a tooth of a patient to restore the tooth, said dental restoration device comprising:

first and second tubular members each having inner and outer peripheral surfaces, said second tubular member being telescopingly movably located with said first tubular member so that said outer peripheral surface of said second tubular member slides along said inner peripheral surface of said first tubular member;

first and second transverse walls of said first and second tubular members, respectively, said first and second transverse walls each being approximately circular in cross-section, said first transverse wall being integrally connected to said first tubular member at or near a first end of said first tubular member, and said second transverse wall being integrally connected to said second tubular member at said first end of said second tubular member;

first and second compartments located within said first and second tubular members, respectively, said first compartment initially containing a powder component of an unmixed dental restoration material and said second compartment initially containing a liquid component of said unmixed dental restoration material;

first and second aperture forming portions located in said first and second transverse walls, respectively, of said first and second tubular members, respectively;

first and second notches being approximately circular in cross-section and being located in said first and second transverse walls, respectively, to define outer boundaries of said first and second aperture forming portions, respectively;

a nozzle connected to said first end of said first tubular member, said nozzle having a rear end portion which has a shape complementarily corresponding to said first end of said first tubular member;

a plunger being approximately cylindrical in cross-section, having a rod-like projection with a blunt leading end at a first end thereof, and being telescopingly movably located within said second tubular member so that when said plunger is moved forwardly towards said second transverse wall of said second tubular member, said blunt leading end of said rod-like projection contacts said second aperture forming portion to detach a portion of said second notch and bend said second aperture forming portion to a position approximately perpendicular to said second transverse wall to form a liquid component outlet hole in said second transverse wall for said liquid component to flow out of said second compartment of said second tubular member into said first compartment of said first tubular member to mix said liquid component of said unmixed dental restoration material with said powder component of said dental restoration material and thereby form a mixed dental restoration material, and then when said plunger is moved farther forwardly towards said first transverse wall of said first tubular member, said blunt leading end of said rod-like projection contacts said first aperture forming portion to detach a portion of said first notch and bend said first aperture forming portion to a position approximately perpendicular to said first transverse wall to form a mixed dental restoration material outlet hole in said first transverse wall of said first tubular member for said mixed dental restoration material to flow out of said first compartment of said first tubular member into said nozzle; and a convex stopper located on a second end of said second tubular member, said convex stopper having a size so as to inhibit said second tubular member from readily sliding completely into said first tubular member when said second aperture forming portion is being bent to form said liquid component outlet hole, but said size of said convex stopper is small enough so as to not inhibit said second tubular member from sliding into said first tubular member when a large force is applied.

2. The dental restoration device as claimed in claim 1, further comprising an applier engagement groove which is recessed into said outer peripheral surface of said first tubular member near a second end of said first tubular member.

3. The dental restoration device as claimed in claim 2, wherein said mixed dental restoration material outlet hole formed by detaching a portion of said first aperture forming portion from said first transverse wall of said first tubular member and said liquid component outlet hole formed by detaching a portion of said second aperture forming portion from said second transverse wall of said second tubular member are each an approximately circular hole, and said first and second notches defining said first and second aperture forming portions, respectively, are approximately three-fourth of a circumference of said mixed dental restoration material outlet hole and said liquid component outlet hole, respectively.

4. The dental restoration device as claimed in claim 1, wherein said mixed dental restoration material outlet hole formed by detaching a portion of said first aperture forming portion from said first transverse wall of said first tubular member and said liquid component outlet hole formed by detaching a portion of said second aperture forming portion from said second transverse wall of said second tubular member are each an approximately circular hole, and said first and second notches defining said first and second aperture forming portions, respectively, are approximately three-fourth of a circumference of said mixed dental restoration material outlet hole and said liquid component outlet hole, respectively.

5. The dental restoration device as claimed in any one of claims 1 to 4, wherein said nozzle is curved and tapers from said rear end portion to a front end portion thereof.

6. The dental restoration device as claimed in claim 5, wherein said rear end portion of said nozzle is connected to said first end of said first tubular member via an engagement of a ring-like convex portion with a ring-like concave portion, said ring-like concave portion having a complementarily corresponding shape to said ring-like convex portion.

7. The dental restoration device as claimed in any one of claims 1 to 4, wherein said rear end portion of said nozzle is connected to said first end of said first tubular member via an engagement of a ring-like convex portion with a ring-like concave portion, said ring-like concave portion having a complementarily corresponding shape to said ring-like convex portion.

* * * * *